(12) United States Patent
Kawai et al.

(10) Patent No.: US 8,672,481 B2
(45) Date of Patent: Mar. 18, 2014

(54) APPARATUS FOR MEASURING OCULAR AXIAL LENGTH

(75) Inventors: Noriji Kawai, Aichi (JP); Masakazu Endo, Aichi (JP)

(73) Assignee: Nidek Co., Ltd., Aichi (JP)

( * ) Notice: Subject to any disclaimer, the term of this patent is extended or adjusted under 35 U.S.C. 154(b) by 342 days.

(21) Appl. No.: 12/977,520

(22) Filed: Dec. 23, 2010

(65) Prior Publication Data

US 2011/0157554 A1    Jun. 30, 2011

(30) Foreign Application Priority Data

Dec. 29, 2009    (JP) ................................. 2009-299155

(51) Int. Cl.
 *A61B 3/14*    (2006.01)
 *A61B 3/00*    (2006.01)
 *A61B 3/10*    (2006.01)

(52) U.S. Cl.
 USPC ............ 351/208; 351/200; 351/205; 351/210

(58) Field of Classification Search
 USPC .......... 351/208, 200, 205, 206, 207, 210, 211
 See application file for complete search history.

(56) References Cited

U.S. PATENT DOCUMENTS

| | | | |
|---|---|---|---|
| 6,779,891 B1 | 8/2004 | Barth et al. | |
| 7,455,406 B2 | 11/2008 | Miwa et al. | |
| 2006/0209259 A1 | 9/2006 | Baikoff | |
| 2007/0002277 A1 | 1/2007 | Hanebuchi | |
| 2008/0151188 A1* | 6/2008 | Kawai et al. | 351/206 |
| 2009/0164007 A1 | 6/2009 | Van Heugten | |
| 2010/0198074 A1* | 8/2010 | Satake | 600/449 |
| 2010/0201946 A1 | 8/2010 | Murakaimi | |

FOREIGN PATENT DOCUMENTS

| | | |
|---|---|---|
| EP | 1905360 A1 | 4/2008 |
| JP | 2002531205 T | 9/2002 |
| JP | 2005160694 A | 6/2005 |
| JP | 2008086527 A | 4/2008 |
| JP | 2010184049 A | 8/2010 |

OTHER PUBLICATIONS

European Search Report for EP 10196858, mailed May 2, 2011.

* cited by examiner

*Primary Examiner* — Dawayne A Pinkney
(74) *Attorney, Agent, or Firm* — Rankin, Hill & Clark LLP (57) ABSTRACT

An object of one aspect of the present invention is to obtain a measurement value in accordance with the condition of a crystalline lens of an examinee's eye. An apparatus for measuring ocular axial length includes: a measuring unit which irradiates measurement waves toward a fundus of the examinee's eye, and calculates the ocular axial length of the examinee's eye based on detection signals obtained from reflected waves including waves reflected from the fundus; and a determining unit which acquires reflection information related to an anterior segment of the examinee's eye, extracts reflection signals corresponding to a reflection object between a cornea and a posterior capsule of a crystalline lens based on the acquired reflection information, and determines whether the examinee's eye is a phakic eye or an IOL eye based on the extracted reflection signals.

10 Claims, 4 Drawing Sheets

APPARATUS FOR MEASURING OCULAR AXIAL LENGTH

CROSS-REFERENCE TO RELATED APPLICATION

This application is based on Japanese Patent Application No. 2009-299155 filed with the Japan Patent Office on Dec. 29, 2009, the entire content of which is hereby incorporated by reference.

BACKGROUND

1. Technical Field

The present invention relates to an apparatus for measuring ocular axial length which measures the ocular axial length of an examinee's eye.

2. Related Art

An apparatus for measuring ocular axial length, which measures the ocular axial length of an examinee's eye by irradiating the cornea and fundus of the examinee's eye with light or ultrasound waves, is known (for example, refer to Patent Document 1).

Documents that describe the related art are listed below.
Patent Document 1: JP 2002-531205 A (PCT)
Patent Document 2: JP 2005-160694 A
Patent Document 3: JP 2008-86527 A

SUMMARY

However, a conventional apparatus could not distinguish the condition of the crystalline lens of the examinee's eye (in other words, whether the examinee's eye is a phakic eye, or an intraocular lens-implanted eye (IOL eye)). Therefore, a conventional apparatus may produce inaccurate measurement results of the ocular axial length because a substance present in the eye differs depending on the condition of the crystalline lens. If the substance present in the eye is different, the refraction index of the eye and the propagation velocity of ultrasound waves would also be different. Thus, in a conventional apparatus, regardless of whether light or ultrasound waves were used as the measurement probe, the ocular axial length could not be accurately measured.

A technical object in one aspect of the present invention is to provide an apparatus for measuring ocular axial length which can obtain a measurement value in accordance with the condition of a crystalline lens of an examinee's eye.

In order to solve the above problem, one aspect of the present invention includes the following configuration.

An apparatus for measuring ocular axial length includes: a measuring unit having a first irradiating system which irradiates measurement waves onto a fundus of an examinee's eye through a cornea of the examinee's eye, a first detector which detects reflected waves including waves reflected from the fundus, and a first calculation part which calculates ocular axial length of the examinee's eye based on detection signals output from the first detector, wherein the first calculation part acquires reflection information related to an anterior segment of the examinee's eye, extracts reflection signals corresponding to a reflection object between the cornea and a posterior capsule of a crystalline lens of the examinee's eye based on the acquired reflection information, and determines whether the examinee's eye is a phakic eye or an IOL eye based on the extracted reflection signals.

According to one embodiment of the present invention, a measurement value in accordance with the condition of the crystalline lens of an examinee's eye can be obtained.

BRIEF DESCRIPTION OF THE DRAWINGS

The foregoing and other objects, features, aspects and advantages of the invention will become more apparent from the following detailed description when taken in conjunction with the accompanying drawings, in which.

DESCRIPTION OF EMBODIMENTS

Preferred embodiments of the present invention will be described below with reference to the accompanying drawings, in which like reference characters designate similar or identical parts throughout the several views thereof.

Figure 1:
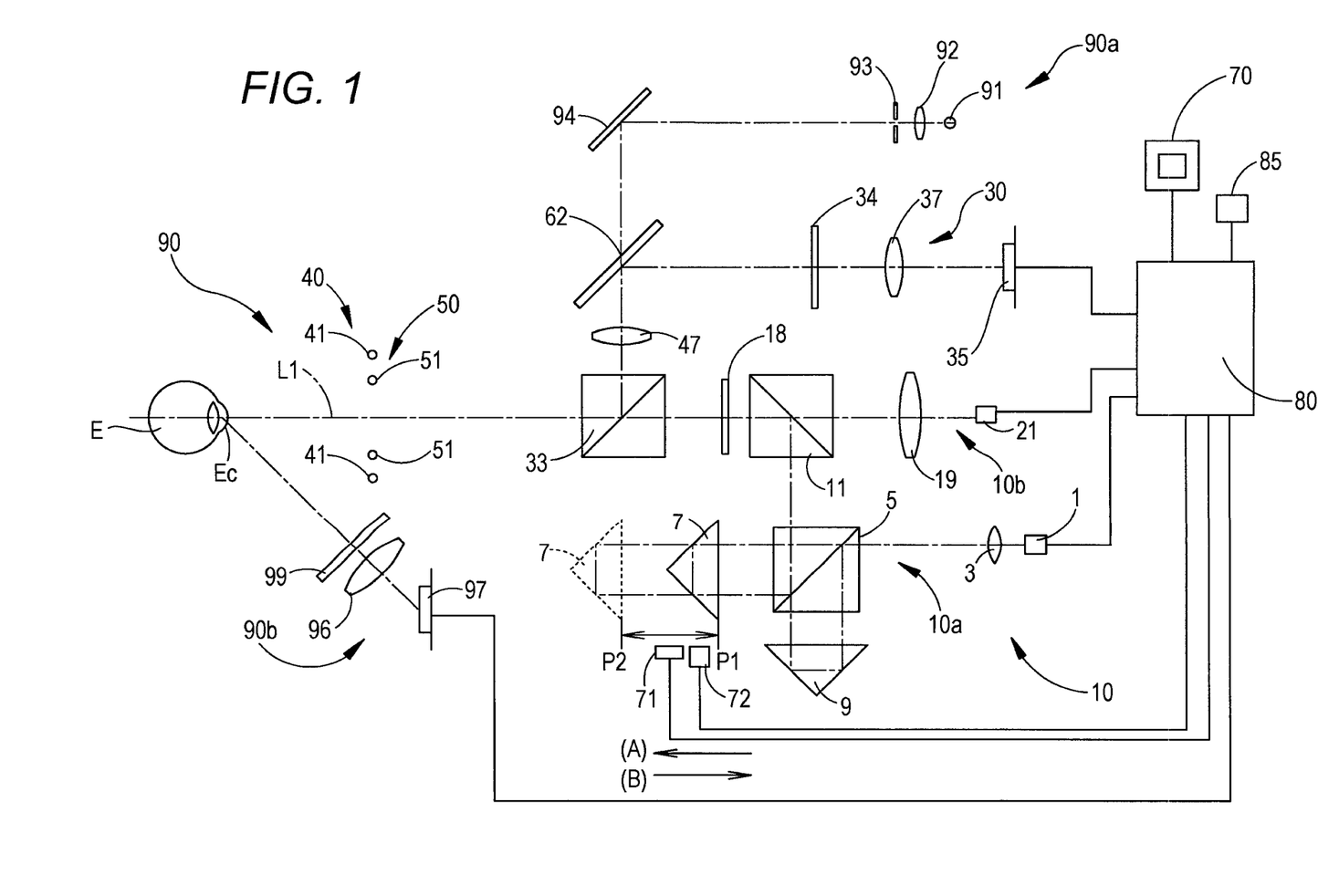
FIG. 1 is a view illustrating a schematic configuration of an optical system and a control system in the present apparatus.

An embodiment of the present invention will be described below based on the drawings. FIG. 1 is a view illustrating a schematic configuration of an optical system of an apparatus for measuring ocular axial length. The optical system is broadly classified into an ocular axial length measuring optical system (measuring unit) 10, a kerato-projecting optical system 40, an alignment projecting optical system 50, an anterior segment front surface imaging optical system 30, and an anterior segment cross-sectional image imaging optical system 90. The kerato-projecting optical system 40 projects a target for measuring the shape of the cornea onto the cornea of an examinee's eye. The anterior segment front surface imaging optical system 30 images an anterior segment front surface image. The anterior segment cross-sectional image imaging optical system 90 images an anterior segment cross-sectional image of the examinee's eye. This optical system is built into a casing which is not illustrated. The casing is driven by a well-known alignment shifting mechanism via an operation member (for example, a joystick). Thereby, the casing is moved in three dimensions with respect to the examinee's eye.

The projecting optical system 40 has a ring-shaped light source 41 disposed with a measurement optical axis L1 as the center. The projecting optical system 40 is used for measuring the shape of the cornea (curvature, astigmatic axial angle, and the like) by projecting a ring target on the cornea of the examinee's eye. As the light source 41, for example, an LED (light-emitting diode) which generates infrared light or visible light is used. The projecting optical system 40 only needs to include at least 3 or more point light sources which are arranged on the same circle centered on the optical axis L1. The light source may be an intermittent ring light source. Further, the projecting optical system 40 may be a placido target projecting optical system which projects a plurality of ring targets.

The alignment projecting optical system 50 has a projection light source 51 which generates infrared light (for example, $\lambda$=970 nm) and is disposed inside the light source 41. The light source 51 is used for projecting an alignment target on the cornea of the examinee's eye. The alignment target projected on the cornea is used for alignment with respect to the examinee's eye (for example, auto-alignment, alignment detection, manual alignment, and the like). In the present embodiment, the projecting optical system 50 is an optical system which projects a ring target on the cornea of the examinee's eye. The ring target is also used as a Mayer ring. The light source 51 of the projecting optical system 50 is also used as an anterior segment light for illuminating the anterior segment by infrared light from a diagonal direction. An optical system which projects parallel light on the cornea may be further provided to the projecting optical system 50. In this configuration, alignment can also be carried out in the front-rear direction by combining the parallel light with finite light from the projecting optical system 50.

The anterior segment front surface imaging optical system 30 is used for imaging an anterior segment front surface image of the examinee's eye. The imaging optical system 30 has a dichroic mirror 33, an objective lens 47, a dichroic mirror 62, a filter 34, an imaging lens 37, and a two-dimensional imaging device 35.

Anterior segment reflection light, which is obtained when light from the projecting optical system 40 and the projecting optical system 50 described above is reflected at the anterior segment, is formed into an image by the two-dimensional imaging device 35 via the dichroic mirror 33, the objective lens 47, the dichroic mirror 62, the filter 34, and the imaging lens 37.

The ocular axial length measuring optical system 10 has a light projecting optical system 10a and a light receiving optical system 10b. The light projecting optical system 10a includes a measurement light source 1, a collimator lens 3, a beam splitter 5, a first triangular prism (corner cube) 7, a second triangular prism 9, a polarizing beam splitter 11, and a quarter wavelength plate 18. The measurement light source 1 is a light source which emits low coherent light (in the present embodiment, it is also a fixation lamp). The collimator lens 3 makes a light flux emitted from the measurement light source 1 into a parallel light flux. The beam splitter 5 splits light emitted from the light source 1. The first triangular prism 7 is disposed in the transmission direction of the beam splitter 5. The second triangular prism 9 is disposed in the reflection direction of the beam splitter 5.

Light (linearly polarized light) emitted from the light source 1 is collimated by the collimator lens 3, and then split by the beam splitter 5 into a first measurement light (reference light) and a second measurement light. The first measurement light is reflected by the triangular prism 7 and bent back. Meanwhile, the second measurement light is reflected by the triangular prism 9 and bent back. Subsequently, the first measurement light and the second measurement light are combined by the beam splitter 5. The combined light is reflected by the polarizing beam splitter 11, and then converted to circularly polarized light by the quarter wavelength plate 18. Then, at least the cornea and fundus of the examinee's eye are irradiated with the circularly polarized light via the dichroic mirror 33. At this time, when the measurement light flux including the circularly polarized light is reflected by the cornea and fundus of the examinee's eye, the phase of the light flux is displaced by ½ a wavelength.

The light receiving optical system 10b is disposed for receiving light (interference light) obtained by the interference of cornea reflection light, which is obtained when measurement light irradiated by the light projecting optical system 10a is reflected at the cornea, and fundus reflection light, which is obtained when measurement light is reflected at the fundus. The light receiving optical system 10b includes the dichroic mirror 33, the quarter wavelength plate 18, the polarizing beam splitter 11, a condenser lens 19, and a light receiving device 21.

The cornea reflection light and the fundus reflection light pass through the dichroic mirror 33, and then are converted to linearly polarized light by the quarter wavelength plate 18. Subsequently, the two reflection lights having passed through the polarizing beam splitter 11 are condensed by the condenser lens 19 and then received by the light receiving device 21.

The triangular prism 7 is used as an optical-path-length changing member for changing the optical path length. The triangular prism 7 is moved linearly relative to the beam splitter 5 along the optical axis direction by the driving of a driving part 71 (for example, a motor). The optical-path-length changing member may also be a triangular mirror. The position of the prism 7 during driving is detected by a position detecting sensor 72 (for example, a potentiometer, an encoder, and the like).

In the above explanation, a configuration in which the cornea reflection light and the fundus reflection light are made to interfere has been described. However, this configuration is not absolutely necessary. In other words, the apparatus for measuring ocular axial length of the present invention may include an optical interference optical system including a beam splitter (light splitting member) which splits light emitted from a light source, a sample arm, a reference aim, and a light receiving device which receives interference light. In this optical interference optical system, interference light obtained by the interference of measurement light with which the examinee's eye is irradiated via the sample arm and reference light from the reference arm is received by the light receiving device. In this case, the optical-path-length changing member is disposed on at least one of the sample arm and the reference arm. If the position of the fundus is detected by reflection light from the fundus, the ocular axial length is roughly measured even if the reflection light from the cornea is not detected.

In the above explanation, a configuration in which the optical path length of reference light is changed by linearly moving the prism 9 has been described. However, this configuration is not absolutely necessary. For example, the apparatus for measuring ocular axial length of the present invention may have a configuration in which the optical path length of reference light is changed by an optical delay mechanism via a rotating reflector (for example, refer to JP 2005-160694 A).

The anterior segment cross-sectional image imaging optical system 90 includes a light projecting optical system 90a and a light receiving optical system 90b. The light projecting optical system 90a projects, on an examinee's eye E, a slit light for forming an anterior segment cross-sectional image. The light receiving optical system 90b receives anterior segment reflection light (anterior segment scattered light) obtained when the slit light projected by the light projecting optical system 90a is reflected at the anterior segment, and then images an anterior segment cross-sectional image.

The light projecting optical system 90a includes a light source 91, a condenser lens 92, a slit plate 93, a total reflection mirror 94, the objective lens 47, and the dichroic mirror 33.

The light receiving optical system 90b includes a two-dimensional imaging device 97 and an imaging lens 96. The imaging lens 96 leads anterior segment reflection light, obtained when light from the light projecting optical system 90a is reflected at the anterior segment, to the imaging device 97. The light receiving optical system 90b has a configuration which images an anterior segment cross-sectional image based on the Scheimpflug principle. Basically, the light receiving optical system 90b is arranged so that its optical axis (imaging optical axis) intersects with the optical axis of the light projecting optical system 90a at a prescribed angle. The light cross-section of the projection image by the light projecting optical system 90a, the lens system (cornea and the imaging lens 96) including the cornea of the examinee's eye, and the imaging surface of the imaging device 97 are arranged so that they are in a Scheimpflug relationship. A filter 99 is disposed on the front side (the examinee's eye E side) of the lens 96. Among the light emitted from the light source 91, the filter 99 passes only light (blue light) used for imaging an anterior segment cross-sectional image.

Next, a control system will be described. A control part 80 performs control of the entire apparatus and calculation of measurement results. The control part 80 is connected to the light source 1, the light source 91, the light source 51, the light source 41, the imaging device 21, the imaging device 35, the imaging device 97, a monitor 70, and the like.

The operation of the apparatus including the configuration described above will be described below. When a trigger signal for measurement initiation is output automatically or manually, the measurement light source 1 is illuminated by the control part 80. Thereby, the examinee's eye is irradiated with a measurement light by the ocular axial length measuring optical system 10. A reflection light obtained when the measurement light is reflected by the examinee's eye then enters the light receiving device 21 of the light receiving optical system 10b.

The control part 80 reciprocatingly moves the first triangular prism 7 by controlling the driving of the driving part 71. The control part 80 calculates the ocular axial length based on the timing at which interference light is detected by the light receiving device 21.

In the case of reciprocating movement, the control part 80 acquires a first interference signal output from the light receiving device 21 when the first triangular prism 7 is moved in a first direction (A direction). The control part 80 acquires a second interference signal output from the light receiving device 21 when the first triangular prism 7 is moved in a second direction (B direction) opposite to the first direction. The control part 80 measures the ocular axial length of the examinee's eye based on the first interference signal and measures the ocular axial length of the examinee's eye based on the second interference signal.

The control part 80 acquires the first interference signal output from the light receiving device 21 when the prism 7 is moved in the A direction. The control part 80 obtains a first measurement result of the ocular axial length based on the position of the prism 7 when the first interference signal is acquired. The control part 80 acquires the second interference signal output from the light receiving device 21 when the prism 7 is moved in the B direction. The control part 80 obtains a second measurement result of the ocular axial length based on the position of the prism 7 when the second interference signal is acquired. Thereby, the ocular axial length of the examinee's eye can be measured twice during one reciprocating movement of the prism 7. Therefore, smooth continuous measurement is possible.

Information (measurement results) that has been acquired regarding the ocular axial length of the examinee's eye is stored in a memory 85. After a prescribed number of measurements have been completed (or after a prescribed number of values of the ocular axial length of the examinee's eye have been obtained), the control part 80 ends the reciprocating movement of the prism 7 and returns the position of the prism 7 to its initial position.

The measurement values of ocular axial length obtained by the above operation are calculated under the condition that the examinee's eye is a phakic eye. Therefore, in measurements of aphakic eyes and intraocular lens (hereinafter called IOL) eyes, the measurement values need to be corrected since changes in the refraction index occur due to differences in the intraocular medium.

Correction of the measurement values will be described below. In this correction, the control part 80 acquires reflection information of the anterior segment of the examinee's eye, and determines the condition of the crystalline lens of the examinee's eye based on the reflection information. The reflection information is, for example, an anterior segment cross-sectional image of the examinee's eye. The control part 80 then calculates a corrected ocular axial length by correcting the measurement value based on the refraction index in accordance with the determined condition of the crystalline lens.

Here, the control part 80 extracts a reflection signal which corresponds to a reflection object present between the cornea and the posterior capsule of the crystalline lens based on the acquired anterior segment cross-sectional image. The reflection object is, for example, a crystalline lens or an IOL. The control part 80 then determines whether the examinee's eye is a phakic eye, an IOL eye, or an aphakic eye based on the extracted reflection signal (refer to FIGS. 3A to 3C and 4). The reflection signal is, for example, the luminance distribution of the anterior segment cross-sectional image or an edge of this luminance distribution.

The correction of the measurement value will be described more specifically below. The control part 80 first images the anterior segment cross-sectional image as reflection information using the imaging optical system 90. In other words, the control part 80 uses the anterior segment front surface imaging optical system 30 to carry out alignment of the measurement optical axis L1 and the examinee's eye. Subsequently, when a trigger signal for carrying out anterior segment cross-section imaging is generated, the control part 80 illuminates the light source 91. Light from the light source 91 is condensed by the condenser lens 92, and then passes through the slit plate 93 to become a slit light. The slit light is reflected at the total reflection mirror 94, passes through the dichroic mirror 62, and then is made into a substantially parallel light flux by the objective lens 47 and reflected at the dichroic mirror 33. The slit light is then condensed on the anterior segment to form a slit cross-sectional image (anterior segment cross-sectional image) on the anterior segment. The anterior segment cross-sectional image is imaged by the imaging device 97 via the filter 99 and the lens 96.

Next, the control part 80 determines the condition of the crystalline lens by performing image processing of the anterior segment cross-sectional image imaged by the above-described operation. For example, the control part 80 calculates the position and thickness of the cornea and the crystalline lens in order to determine the condition of the crystalline lens.

Figure 2A:
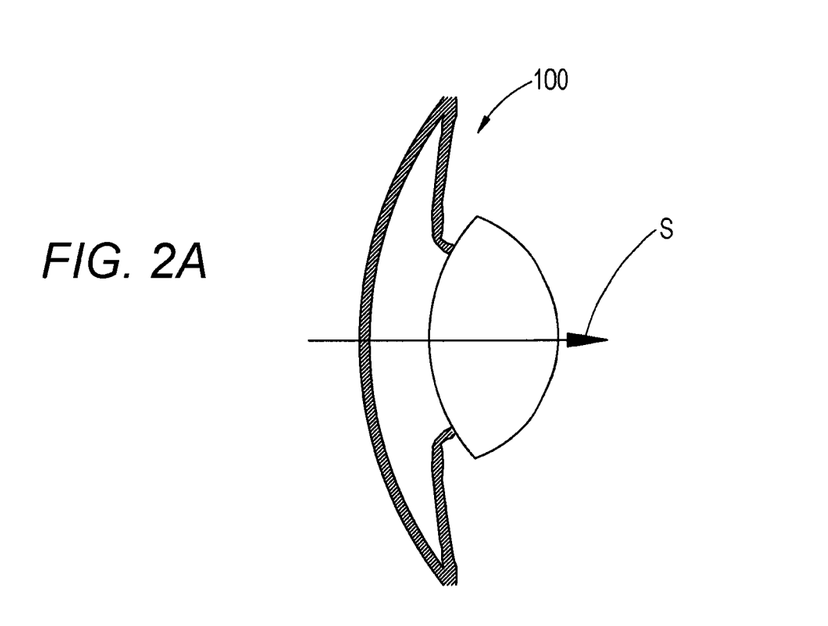
FIGS. 2A and 2B are views illustrating anterior segment cross-sectional images, and luminance distributions obtained when the anterior segment cross-sectional images are scanned in the direction of the Z axis.
Figure 2B:
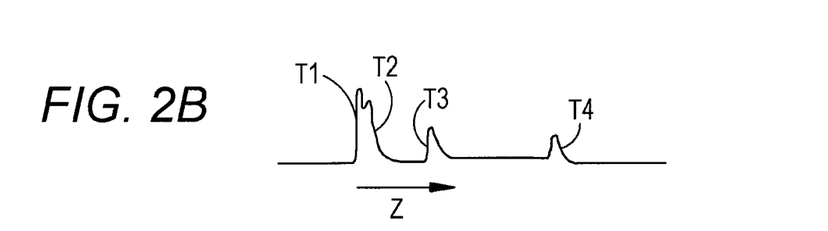

The calculation method will now be described. First, as shown in FIGS. 2A and 2B, the control part 80 scans the center of an anterior segment cross-sectional image (refer to FIG. 2A) 100, which has been imaged, in the Z axis direction (refer to S in FIG. 2A). Thereby, the control part 80 obtains the luminance distribution of the anterior segment cross-sectional image (refer to FIG. 2B). The control part 80 then detects the edges of the luminance distribution. In other words, the control part 80 detects a rise (first edge) T1, a fall (second edge) T2, a rise (third edge) T3, and a fall (fourth edge) T4. Thereby, a reflection signal, which corresponds to a reflection object present between the cornea and the posterior capsule of the crystalline lens, is extracted.

Figure 3A:
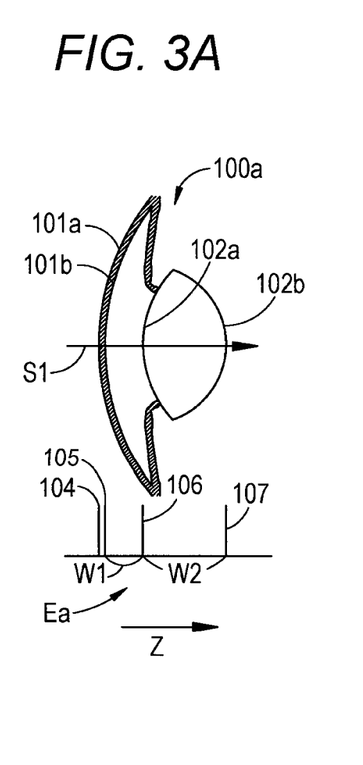
FIGS. 3A to 3C are views illustrating anterior segment cross-sectional images and edge detection results for different crystalline lens conditions.
Figure 3B:
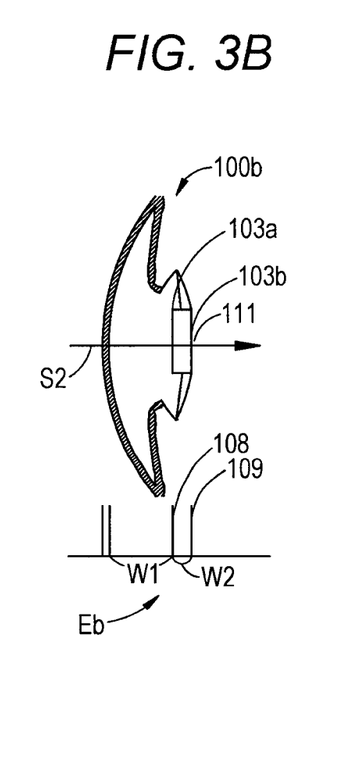
Figure 3C:
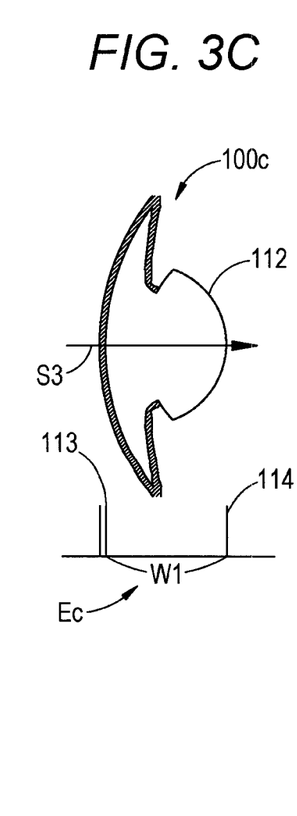

The relationship between the anterior segment cross-sectional image and the luminance distribution will now be described. FIGS. 3A to 3C illustrate the relationships between the anterior segment cross-sectional images of eyes having different crystalline lens conditions and the results of edge detection of the luminance distributions thereof. FIG. 3A illustrates an anterior segment cross-sectional image $100a$ in the case that the examinee's eye is a phakic eye, and an edge detection result Ea of the luminance distribution obtained by scanning the center of the anterior segment cross-sectional image $100a$ in the Z axis direction (refer to S1 in FIG. 3A). As shown in this drawing, a total of four edges can be detected by analyzing the edge detection results along the Z axis direction. A first edge 104 corresponds to the position of a cornea anterior surface $101a$. A second edge 105 corresponds to a cornea posterior surface $101b$ of the examinee's eye. A third edge 106 corresponds to an anterior surface $102a$ of a crystalline lens. A fourth edge 107 corresponds to a posterior capsule $102b$ of the crystalline lens (a posterior surface of the crystalline lens). The thickness of the crystalline lens in the phakic eye is approximately 4 mm by actual measurement conversion. Therefore, the edge detection result Ea shown in FIG. 3A has a characteristic feature in that an interval (thickness of the crystalline lens) W2 between the third edge 106 and the fourth edge 107 is approximately 4 mm.

Next, FIG. 3B illustrates an anterior segment cross-sectional image $100b$ in the case that the examinee's eye is an IOL eye, and an edge detection result Eb of the luminance distribution obtained by scanning the center of the anterior segment cross-sectional image $100b$ in the Z axis direction (S2). In the IOL eye, since the anterior surface of the crystalline lens is excised by surgery, the anterior surface of the crystalline lens does not exist. Therefore, a third edge 108 corresponds to an IOL anterior surface $103a$. A fourth edge 109 corresponds to an IOL posterior surface $103b$. In the IOL eye, a posterior capsule 111 of the crystalline lens remains, but is in contact with the IOL posterior surface. In the IOL eye, therefore, a total of four edges are detected. The thickness of an IOL is approximately 0.5 mm to 1.0 mm, and thus is greatly different from the thickness of the crystalline lens shown in FIG. 3A. Therefore, the edge detection result Eb shown in FIG. 3B has a characteristic feature in that an interval (thickness of the IOL) W2 between the third edge 108 and the fourth edge 109 is approximately 0.5 mm to 1.0 mm.

FIG. 3C illustrates an anterior segment cross-sectional image $100c$ in the case that the examinee's eye is an aphakic eye, and an edge detection result Ec of the luminance distribution obtained by scanning the center of the anterior segment cross-sectional image $100c$ in the Z axis direction (S3). In the aphakic eye, the anterior surface of the crystalline lens does not exist, and only a posterior capsule 112 of the crystalline lens remains. Further, an IOL also does not exist in the aphakic eye. Therefore, a third edge 114 corresponds to the posterior capsule 112 of the crystalline lens. Further, a fourth edge is not found. Therefore, in the aphakic eye, a total of three edges are detected. Since the anterior surface of the crystalline lens does not exist in the aphakic eye, in FIG. 3C, a characteristic feature can be seen in that an interval W1 between a second edge 113 and the third edge 114 is larger than the intervals W1 shown in FIGS. 3A and 3B.

Based on the features discussed above, the actual correction operation will be described below using the flowchart in FIG. 4. After imaging of the anterior segment cross-sectional image is complete, the control part 80 scans the center of the anterior segment cross-sectional image which has been imaged in the Z axis direction. Thereby, the control part 80 obtains the luminance distribution of this image. Subsequently, the control part 80 detects the edges of the luminance distribution. After the control part 80 completes the edge detection across the entire region of the luminance distribution, the control part 80 determines to which area of the examinee's eye each edge corresponds. The control part 80 then determines the condition of the crystalline lens of the examinee's eye based on the determination result.

The control part 80 determines whether or not the interval W1 between the second edge and the third edge is equal to or greater than a prescribed interval Wa (in the present embodiment, approximately 7 mm by actual measurement conversion). If the interval W1 which is actually measured and converted is equal to or greater than Wa, the control part 80 determines that the examinee's eye is an aphakic eye. The reason for this determination is that, as shown in FIG. 3C, in a measurement on an aphakic eye, since the anterior surface of the crystalline lens does not exist, the third edge corresponds to the posterior capsule of the crystalline lens, and thus the interval W1 between the second edge and the third edge is larger than that of a phakic eye or an IOL eye. If the interval W1 between the second edge and the third edge is not equal to or greater than Wa, the control part 80 proceeds to the next determination.

In the next determination, the control part 80 determines whether the interval W2 between the third edge and the fourth edge is substantially equal, by actual measurement conversion, to a prescribed interval Wb (in the present embodiment, approximately 4 mm by actual measurement conversion). If the interval W2 between the third edge and the fourth edge is substantially equal to Wb, the control part 80 determines that the examinee's eye is a phakic eye. The reason for this determination is that such an interval W2, as described using FIG. 3A, corresponds to the thickness of the crystalline lens (approximately 4 mm by actual measurement conversion). If the interval W2 between the third edge and the fourth edge is not substantially equal to Wb, then the control part 80 proceeds to the next determination.

In the next determination, the control part 80 determines whether the interval W2 between the third edge and the fourth edge is between prescribed intervals Wc to Wd (in the present embodiment, approximately 0.5 mm to 1.0 mm by actual measurement conversion). If the interval W2 between the third edge and the fourth edge is between Wc to Wd, the control part 80 determines that the examinee's eye is an IOL eye. The reason for this determination is that such an interval W2, as shown in FIG. 3B, corresponds to the thickness of an IOL (approximately 0.5 mm to 1.0 mm).

In the above-described determinations, if the interval W1 is not equal to or greater than the prescribed interval Wa, and the interval W2 is not substantially equal to Wb, and further the interval W2 is not between Wc to Wd, or if an edge is not detected, the control part 80 performs scanning again to obtain the luminance distribution. Subsequently, the control part 80 detects the edges and carries out the determinations again.

In the present embodiment, the control part 80 determines the condition of the crystalline lens by the intervals between the second edge, the third edge, and the fourth edge. However such a determination is not absolutely necessary. In other words, the intervals between the edges which appear due to changes in the condition of the crystalline lens can be used. For example, by simply comparing the intervals between the second edge and the third edge, it is possible to distinguish between a phakic eye, an aphakic eye, and an IOL eye.

In the present embodiment, the control part 80 determines whether the examinee's eye is a phakic eye or an IOL eye based on the intervals of the edges in the reflection signals.

However, such a determination method is not absolutely necessary. For example, the control part 80 may perform the above determinations based on the detection positions of a portion of the reflection signals (for example, the third edge). Further, the control part 80 may also carry out the determinations using both the intervals of the edges and the detection positions of the edges.

Further, regarding the presence or absence of a crystalline lens in the examinee's eye (whether the eye is a phakic eye or an IOL eye, or an aphakic eye), this may be determined based on the total edge number as well. Specifically, the control part 80 determines whether the total edge number found from the luminance distribution is three or four. If the total edge number is three, then the control part 80 determines that the examinee's eye is an aphakic eye. The reason for this determination is that, as described above using FIG. 3C, in an aphakic eye, there is neither anterior surface of the crystalline lens nor an IOL, and only the posterior capsule of the crystalline lens remains, and thus the third edge corresponds to the posterior capsule, not the anterior surface, of the crystalline lens. Therefore, a characteristic feature of an aphakic eye is that a total of only three edges can be detected, corresponding to the three locations of the cornea anterior surface, the cornea posterior surface, and the posterior capsule of the crystalline lens. If the total edge number is four, then the control part 80 determines that the examinee's eye is either a phakic eye or an IOL eye. The reason for this determination is that, as shown in FIGS. 3A and 3B, in a phakic eye, the third edge corresponds to the anterior surface of the crystalline lens and the fourth edge corresponds to the posterior capsule of the crystalline lens, while in an IOL eye, the third edge corresponds to the IOL anterior surface and the fourth edge corresponds to the IOL posterior surface with which the posterior capsule of the crystalline lens is in contact. Therefore, in both a phakic eye and an IOL eye, the total edge number is four. There are some aphakic eyes from which the posterior capsule of the crystalline lens is also removed. In this case, the total edge number may be two. The condition of the crystalline lens is determined as described above.

The present embodiment is not limited to the method described above, and the condition of the crystalline lens can also be determined by using other parts of the cross-sectional image which differ due to differences in the condition of the crystalline lens. For example, the control part 80 makes a determination based on the shape of each reflection surface obtained from the extracted reflection signals. For example, the control part 80 performs edge detection on the entire image, and then calculates the curvature of the reflection surface corresponding to each of the plurality of detected edges. The control part 80 can then determine the condition of the crystalline lens based on this calculation result.

Next, the control part 80 finds the measurement value of the ocular axial length in accordance with the results of determination of the condition of the crystalline lens. The control part 80 then displays the calculation result on a monitor 70. In other words, the control part 80 determines the condition of the crystalline lens based on the edges as described above, and then corrects the measurement value of the ocular axial length in accordance with whether the examinee's eye is a phakic eye, an aphakic eye, or an IOL eye. The ocular axial length is calculated by the following calculation formula: scan distance ($\Delta Z$) of a scan mirror within an interferometer/refraction index of a human eye. The refraction index of a human eye changes depending on the condition of the crystalline lens. Therefore, when calculating the ocular axial length, the control part 80 changes the refraction index of a human eye in accordance with the condition of the crystalline lens. Thereby, the measurement value is corrected.

In more detail, the control part 80 displays the results of determination of the condition of the crystalline lens, determined by the above-described operation, on the monitor 70. If the examinee's eye is not a phakic eye, the control part 80 displays on the monitor 70 a display asking whether it may automatically correct the ocular axial length in accordance with the condition of the crystalline lens. Here, if an examiner selects to perform automatic correction, the control part 80 selects a refraction index of a human eye in accordance with each crystalline lens condition and reflects this in the above-described calculation formula. Thereby, the measurement value of the ocular axial length is corrected. When the correction of the measurement value of the ocular axial length has been completed, the control part 80 displays the measurement value of the ocular axial length on the monitor 70.

The control part 80 may store the measurement result of the ocular axial length before correction (or, of course, the scan distance of the scan mirror) and the determination result of the condition of the crystalline lens in the memory 85. After a certain amount of time has passed, the control part 80 may find the measurement value of the ocular axial length in accordance with the determination result. As long as a measurement result of ocular axial length and a determination result of the condition of the crystalline lens exist, even without the ocular axial length measurement apparatus main body, the measurement value in accordance with the condition of the crystalline lens can be obtained by another apparatus.

In the above-described configuration, the control part 80 can also detect, by the measuring optical system 10, the reflection information of the anterior segment used for determining the condition of the crystalline lens. In this case, the control part 80 extracts reflection signals corresponding to a reflection object present between the cornea and the posterior capsule of the crystalline lens based on interference signals detected when measuring the ocular axial length. A movement range of the scan mirror needs to be secured such that the reflection information of the anterior segment is detected.

An optical scanner for scanning a measurement light on the anterior segment may also be provided to the apparatus for measuring ocular axial length of the present embodiment. In this case, interference light between a measurement light flux reflected at the anterior segment of the examinee's eye and a reference light flux may be received by this scanner. Further, the reflection information of the anterior segment may be detected by an optical interference optical system (OCT optical system) which images a tomographic image of the anterior segment of the examinee's eye.

By the apparatus for measuring ocular axial length of the present embodiment, in addition to the determination of the condition of the crystalline lens described above, it may also be determined whether the examinee's eye is a refractive corrected eye treated using a keratectomy laser (for example, a lasik eye subjected to lasik surgery) based on the reflection information of the anterior segment of the examinee's eye.

In more detail, the control part 80 extracts reflection signals corresponding to the cornea of the examinee's eye based on an anterior segment cross-sectional image that has been acquired. The control part 80 then determines, based on the extracted reflection signals, whether the examinee's eye is a refractive corrected eye that has been treated using a laser beam.

In this determination, the control part 80 acquires a plurality of luminance distributions by performing a plurality of scans in the Z axis direction on the anterior segment cross-sectional image, and then detects the edges corresponding to the cornea in the luminance distributions. The control part 80 then compares the curvature of the cornea in a normal eye that has been found in advance with the curvature of the cornea obtained based on the edge detection. The control part 80 determines that the examinee's eye is a laser refractive corrected eye if a difference equal to or greater than a certain fixed value exists between the two curvatures. The control part 80 then displays the determination result on the monitor 70. If the examinee's eye is a laser refractive corrected eye, the curvature of the cornea will be smaller than that of a normal eye (in the case of myopia correction).

By the above-described process, it is also possible to determine whether the examinee's eye is a refractive corrected eye that has been treated using a laser (hereinafter, a laser refractive corrected eye). If a determination result indicating that the examinee's eye is a laser refractive corrected eye is displayed, the examiner selects an IOL dioptic power calculation formula (Camellin-Calossi formula, Haigis-L formula, Shammas formula, and the like) in accordance with the laser refractive corrected eye. Thereby, an appropriate IOL dioptic power is calculated.

In this case, the control part 80 can calculate the intraocular lens dioptic power using the calculated ocular axial length and the calculation formula stored in the memory 85. As described above, in the case that the examinee's eye is determined to be a laser refractive corrected eye, the control part 80 can select a calculation formula in accordance with the laser refractive corrected eye to calculate the dioptic power. A plurality of calculation formulas (SRK formula, SRK-II formula, SRK/T formula, Camellin-Calossi formula, Haigis-L formula, Shammas formula, and the like) are stored in the memory 85.

The method for determining a laser refractive corrected eye is not limited to the above-described method. It is also possible to determine whether the examinee's eye is a laser refractive corrected eye by using some kind of different parts in the cross-sectional images which are based on differences between a laser refractive corrected eye and a non-laser refractive corrected eye.

For example, such a determination can be carried out by detecting the interval between the first edge 104 corresponding to the cornea anterior surface 101*a* and the second edge 105 corresponding to the cornea posterior surface 101*b* shown in FIG. 3A described above. In other words, the interval between the edges corresponds to the cornea thickness. Therefore, if the interval between the edges is equal to or less than a certain prescribed value, it can be determined that the examinee's eye is a lasik eye.

In the scanning for obtaining the luminance distribution in the present embodiment, when the center is scanned by an optical system, misdetections due to optical noise can occur. Therefore, the luminance distribution may also be obtained by scanning so as to avoid the center and not scan the iris. In this case, the luminance distribution is acquired by scanning an optical system at a position that is slightly offset from the center in the X axis direction (transverse direction). The control part 80 then determines the condition of the crystalline lens (or the cornea) in the examinee's eye by performing edge detection on the luminance distribution. The optical noise mentioned above occurs when scattered light, which is generated when light from the light source 91 passes through an optical member of the light projecting optical system 90*a*, is received by the imaging device 97 via the anterior segment.

Figure 4:
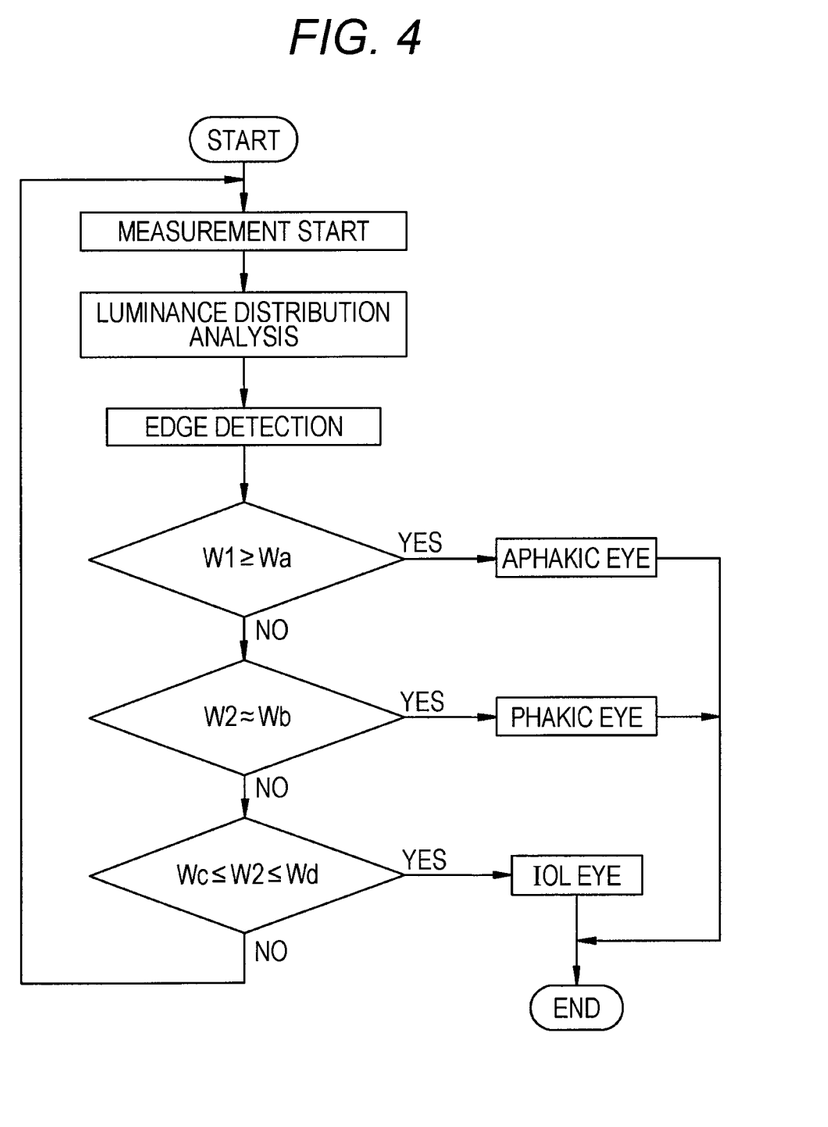
FIG. 4 is a flowchart illustrating a procedure for determining the crystalline lens condition.

It has been described regarding FIG. 4 that if the interval W1 is not equal to or greater than the prescribed interval Wa, and the interval W2 is not substantially equal to Wb, and further the interval W2 is not between Wc to Wd, or if an edge is not detected, the scanning is performed again to acquire the luminance distribution. However, the present invention is not limited to this, and in such a case, the control part 80 may, for example, perform scanning in a depth direction at a plurality of different locations in the X axis direction (transverse direction). The control part 80 may then determine the condition of the crystalline lens using the luminance distributions obtained at each location. In this case, the control part 80 may, for example, perform error determination in order from the luminance distribution near the center. The control part 80 may then determine the condition of the crystalline lens using the luminance distribution determined to be appropriate.

As another aspect of the present invention, it is also possible to realize the present invention as an apparatus for measuring ocular axial length including an A-scan ultrasound probe as a measuring unit which measures the ocular axial length of the examinee's eye (for example, refer to JP 2008-86527 A). In this apparatus, reflection echoes from the cornea and the fundus are received as reflection information of the anterior segment of the examinee's eye by the ultrasound probe which has been contacted with the cornea of the examinee's eye. The ocular axial length is then measured based on the received reflection echoes. In this apparatus, for example, it is possible to detect the edges in the reflection echoes from the anterior segment using the ultrasound probe to determine the condition of the crystalline lens from the intervals between the edges or the like. In this apparatus, the reflection information of the anterior segment may also be detected using a B-scan ultrasound probe.

In the present embodiment, apparatuses for measuring ocular axial length using light or ultrasound waves have been described as an example. However, apparatuses for measuring ocular axial length according to other aspects of the present invention are not limited to this configuration, and can use arbitrary measurement waves. For example, as a measurement wave, it is possible to use electromagnetic waves (electrical radiation, light, X rays, gamma rays, and the like), sound waves (ultrasound waves, acoustic energy, and the like), and the like.

In the present embodiment, the control part 80 determines whether the examinee's eye is a phakic eye, an IOL eye, or an aphakic eye by executing the process shown in FIG. 4. However, the present invention is not limited to this configuration, and the control part 80 may have a configuration to determine only whether the examinee's eye is a phakic eye or an IOL eye. In other words, the examinee's eye is normally either a phakic eye or an IOL eye, and is very unlikely to be an aphakic eye. Therefore, in general, it is possible to accurately measure the ocular axial length by simply distinguishing between a phakic eye and an IOL eye.

While the invention has been illustrated and described in detail, the foregoing description is in all aspects illustrative and not restrictive. It is therefore understood that numerous modifications and variations can be devised without departing from the spirit and scope of the invention.

What is claimed is:

1. An apparatus for measuring ocular axial length, comprising:
    a measuring unit having a first irradiating system which irradiates measurement waves onto a fundus of an examinee's eye through a cornea of the examinee's eye, a first detector which detects reflected waves including waves reflected from the fundus, and a first calculation part which calculates ocular axial length of the examinee's eye based on detection signals output from the first detector, wherein the first calculation part acquires reflection information related to an anterior segment of the examinee's eye, extracts reflection signals corresponding to a reflection object between the cornea and a posterior capsule of a crystalline lens of the examinee's eye based on the acquired reflection information, and determines whether the examinee's eye is a phakic eye or an IOL eye based on the extracted reflection signals.

2. The apparatus for measuring ocular axial length according to claim 1, wherein the first calculation part calculates an ocular axial length value of the examinee's eye in accordance with the determination result.

3. The apparatus for measuring ocular axial length according to claim 2, further comprising:
a monitor which displays the calculated ocular axial length value.

4. The apparatus for measuring ocular axial length according to claim 1, wherein the first calculation part performs the determination using at least one of an interval between the extracted reflection signals and a position of the extracted reflection signals, or performs the determination based on a shape of each reflection surface obtained from the extracted reflection signals.

5. The apparatus for measuring ocular axial length according to claim 1, wherein the first calculation part extracts reflection signals corresponding to an anterior surface of the crystalline lens or an anterior surface of the IOL based on the acquired reflection information, and determines whether the examinee's eye is the phakic eye, or the IOL eye, or an aphakic eye based on the extracted reflection signals.

6. The apparatus for measuring ocular axial length according to claim 1, further comprising:
an anterior segment information acquiring unit,
wherein the anterior segment information acquiring unit comprises:
a second irradiating system which irradiates measurement waves onto the anterior segment;
a second detector which detects waves reflected from the anterior segment; and
a second calculation part which acquires the reflection information based on detection signals output from the second detector, and
the first calculation part acquires the reflection information from the second calculation part.

7. The apparatus for measuring ocular axial length according to claim 6, wherein the first irradiating system is used as the second irradiating system, the first detector is used as the second detector, and the first calculating part is used as the second calculating part.

8. The apparatus for measuring ocular axial length according to claim 6, wherein the anterior segment information acquiring unit has an imaging unit which is used as the second irradiating system and the second detector, the imaging unit images a cross-sectional image of the anterior segment, the second calculating part acquires the reflection information based on a signal of the imaged cross-sectional image.

9. The apparatus for measuring ocular axial length according to claim 1, wherein the first calculation part extracts reflection signals corresponding to the cornea based on the acquired reflection information, and determines, based on the extracted reflection signals, whether the examinee's eye is a refractive corrected eye that has been treated by a laser beam.

10. The apparatus for measuring ocular axial length according to claim 9, further comprising:
a memory which stores a plurality of intraocular lens dioptic power calculation formulas,
wherein the first calculation part calculates an intraocular lens dioptic power using the calculated ocular axial length value and a calculation formula stored in the memory, and when it is determined that the examinee's eye is the refractive corrected eye, the first calculation part selects a calculation formula corresponding to the refractive corrected eye to calculate the intraocular lens dioptic power.

* * * * *